United States Patent [19]

Akins

[11] 4,233,690
[45] Nov. 18, 1980

[54] PROSTHETIC DEVICE COUPLINGS

[75] Inventor: Robert J. Akins, La Mesa, Calif.

[73] Assignee: CarboMedics, Inc., San Diego, Calif.

[21] Appl. No.: 907,664

[22] Filed: May 19, 1978

[51] Int. Cl.³ .............................................. A61F 1/22
[52] U.S. Cl. ......................................................... 3/1.5
[58] Field of Search .................. 3/17 R, 1.5, 1.9, 1.91, 3/1.4, 1.1, 1.7, DIG. 3, 1.5; 128/92 D, 92 R

[56] References Cited

U.S. PATENT DOCUMENTS

| | | | |
|---|---|---|---|
| 3,786,806 | 1/1974 | Johnson et al. | 128/92 D |
| 3,859,668 | 1/1975 | Anderson | 3/1.5 |

FOREIGN PATENT DOCUMENTS 2703529  8/1978  Fed. Rep. of Germany ......... 128/92 B Primary Examiner—E. H. Eickholt
Attorney, Agent, or Firm—Fitch, Even, Tabin, Flannery & Welsh

[57] ABSTRACT

A prosthetic element is securely joined to a natural element of the human body using a ductile metal alloy coupling member which has a transition-temperature range and which has been deformed from its original shape at a temperature below its transition-temperature. Heating the coupling member to a temperature above the transition temperature, as by passing electric current therethrough, causes the coupling to try to return to its original shape and effect a secure joinder.

A prosthetic device for long-term implantation in the human body can be made by using such a coupling element to join a circumscribing member, e.g., a sewing cuff, to a generally tubular, rigid portion of a prosthetic device, e.g., a heart valve body.

3 Claims, 8 Drawing Figures

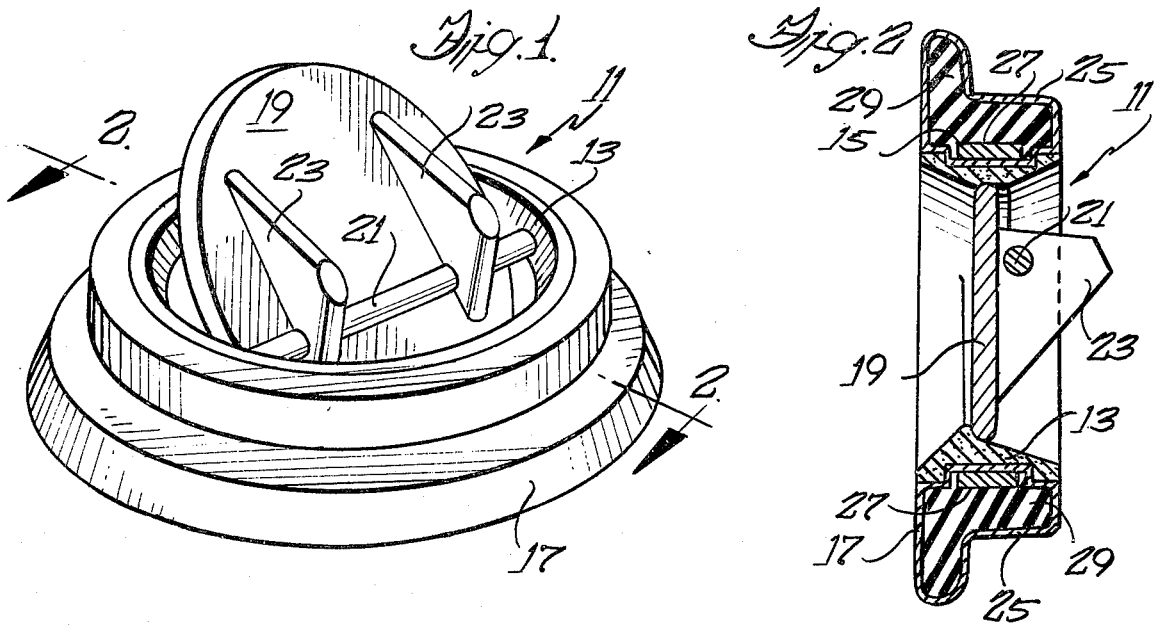

PROSTHETIC DEVICE COUPLINGS

BACKGROUND OF THE INVENTION

This invention relates to prosthetic devices and more particularly to prosthetic devices designed for long-term implantation in the human body wherein it is necessary to make a connection between two components or between a prosthetic element and an element of the human body.

In fabricating prosthetic devices for implantation in the human body, it often becomes necessary to attach dissimilar materials to each other. One example is the attachment of a fabric sewing cuff to the exterior of a housing portion of a heart valve. Heretofore, such fabric sewing cuffs have been attached using a circumferential fabric wrapping, a heat-shrinkable synthetic polymer, or a wrapping of metallic wire. However, because it is now hoped that heart valves and other such prosthetic devices, once implanted within the human body, can stay there for the life of the patient, it is important that the joinder remain excellent over a long period of time. It is also desired to eliminate any possibility of failure as a result of mishandling in any way, as for example by overheating a heat-shrinkable polymer. Moreover, synthetic polymers are inherently subject to creep over their lifetime, and if, for example, a heart valve should ever break loose from the sewing cuff, the possible harm to the patient would be most serious.

SUMMARY OF THE INVENTION

The invention provides a method for securely joining a prosthetic element to a natural element of the human body or to another component of the prosthetic device itself. The invention utilizes a coupling element made from a metal alloy which has the novel property of, upon heating, returning to a precise shape from which it has been deformed at a lower temperature. Nickel-titanium alloys have been developed from approximately equiatomic amounts of nickel and titanium, and these alloys have a transition-temperature range above which they exhibit an inherent shape memory. Thus, by machining such an alloy to a precise shape desired for a particular prosthetic application, cooling the alloy below the transition-temeperature range and deforming the cooled alloy by expansion, contraction or bending, it will return to the precise original shape upon warming above the transition temperature. The precision which such a metal alloy exhibits can be used to important advantage in prosthetic applications.

BRIEF DESCRIPTION OF THE DRAWINGS

Advantages of the invention will be apparent from the following detailed description when read in conjunction with the appended drawings wherein:

FIG. 1 is a perspective view of a heart valve having a sewing cuff attached thereto in a manner embodying various features of the present invention;

FIG. 2 is a sectional view taken generally along line 2—2 of FIG. 1 with the valve member shown in the closed position;

FIG 3 is a perspective view of a blood access device where artificial grafts are attached to the entry and exit ends thereof by coupling elements in accordance with the present invention;

FIG. 4 is a sectional view taken along line 4—4 of FIG. 3;

FIG. 5 demonstrates the connection of an artificial tendon or ligament to a bone which is a part of a living body;

FIGS. 6A and 6B are enlarged fragmentary views illustrating the connection shown in FIG. 5; and FIG. 7 is a fragmentary sectional view generally similar to FIG. 2 showing another method of attachment embodying various features of the present invention.

DESCRIPTION OF THE PREFERRED EMBODIMENTS

Illustrated in FIG. 1 is a pivoting disc heart valve 11 designed for replacement of a defective valve in a human heart. The heart valve 11 includes a rigid housing or body portion 13 of generally tubular shape which has an essentially circular periphery. The housing 13 has a groove 15 formed in the exterior of its side wall. A sewing ring or cuff 17 is attached to the exterior, grooved portion of the side wall and permits the replacement valve 11 to be sutured in place.

The invention is equally applicable to heart valves of various different designs, for example a ball and cage type valve, although a pivoting disc valve is illustrated. A circular disc 19 serves as a valve member and pivots or rotates from an open position to a closed position and back to the open position in response to differential blood pressure. The disc 19 is retained on a shaft 21 which passes through apertures in a pair of support lugs 23. Thus, the disc is free to turn about the shaft 21 as a pivot point which is located as an off-center or eccentric axis with respect to the circular disc 19. The interior portion of the housing 13 is appropriately tapered so as to cooperate with the disc 19 in sealing the valve opening. The construction and operation of the valve 11 is more particularly pointed out in U.S. Pat. No. 3,546,711, issued Dec. 15, 1970.

The fabric sewing ring 17 has an outer covering 25 of a suitable synthetic polymer fabric, prefereably a polyester, such as that sold under the trademark Dacron, which is biocompatible. As seen in FIG. 2, the sewing ring 17 has embedded therein a coupling element 27 made of a nickel-titanium alloy, and disposed exterior thereof there is provided a larger, generally soft ring 29 of a suitable synthetic plastic material, such as a fluorosilicone rubber or some similar semi-rigid polymer that is biocompatible and capable of sterilization.

The coupling element 27 is made of a nickel-titanium alloy of the type marketed under the trademark Nitinol by RayChem, Co. These metal alloys, containing about 50 percent atoms of nickel and about 50 percent atoms of titanium, have a transition-temperature range above which the alloy will return to a precise fabricated shape. Accordingly, the coupling element 27 is formed to the precise shape desired by molding, casting, machining or the like at a temperature above the transition-temperature. The particular transition-temperature range is dependent upon the precise metallic composition of the alloy, and it can be varied in order to tailor the alloy to a particular application. Such a change in transition-temperature range is accomplished in either of two ways: by adding additional nickel in excess of the 50:50 ratio or by substituting a particular atomic amount of cobalt for the same atomic amount of nickel. For a prosthetic device, an alloy is preferably used which becomes ductile at a temperature below normal body temperature, i.e., at about 37° C. or below although alloys having a higher transition temperature may be employed.

Below the transition-temperature range, these metallic alloys exhibit excellent ductility and may be deformed in an amount of up to about 8 percent without inhibiting their ability to return to the precise original configuration. The strain which is introduced by physical deformation at a temperature below the transition-temperature range, is, in effect, a storage of energy, and when the alloy is heated to and through the temperature-transition range, the alloy quickly tries to return to its original shape. Consequently, the coupling element 27 becomes physically entrapped within the groove 15 in the sidewall of the housing from which it cannot escape. By forming the coupling element 27 to precise dimensions, and similarly holding a close tolerance on the exterior dimension of the heart valve housing 13, the fabric covering 25 for the sewing ring is securely squeezed between the coupling element and the rigid groove wall, and the sizing may be such that the ring 27 cannot quite return and thus it will remain with a predetermined amount of tensile stress throughout. The alloy is rigid and unyielding above the transition-temperature range, and advantage can further be taken of this property to create a secure joinder.

After assembly of the coupling element 27 and the fabric covering 25, the semi-rigid ring 29 is installed, and the fabric covering is then enveloped about it and sewn together at a suitable circular seam using standard techniques. This metallurgically homogeneous coupling element 27 joins the sewing ring 17 to the valve body 13 in so secure a manner that there is no reasonable chance of the ring 17 parting from the housing 13 even after years of implantation in the body of the patient.

Shown in FIG. 3 is a blood access device 31 which is designed to be semi-permanently implanted in the body, for example, in one's arm, in order to facilitate repeated entry into the bloodstream of a patient. For example, such a device allows repeated withdrawing or injection of blood into the patient over a prolonged period. One illustrative device of this sort is shown in U.S. Pat. No. 4,015,601 issued to Bokros and Slivenko on Apr. 5, 1977. The preferred way of installing such a blood access device 31 is to provide it with short vascular grafts 33 which can be appropriately sutured to the circulatory system of the body. The present invention provides a way for coupling these vascular grafts 33 to rigid tubular portions or connectors 35 which form a part of the lower portion of the blood access device 31.

As best seen in FIG. 4, the vascular grafts 33 are sized to just fit over the exterior surface of the tubular portions 35 of the blood access device, and preferably a shallow depression or groove 37 is provided adjacent the end of each of the tubular portions. A coupling element 39 is formed in the shape of a ring, from a nickel-titanium alloy, having an inner diameter just sufficiently larger than the groove diameter to allow for the wall thickness of the end portion of the vascular graft 33 in a totally compressed condition.

When the coupling 39 is cooled to a temperature below its transition-temperature range, it becomes ductile, and it is then uniformly expanded to a size just large enough to allow it to slip onto the end of the vascular graft 33 after it has been installed on the tubular portion 35 of the blood access device. By heating the coupling element 39 back above its transition-temperature range, the expanded metal alloy ring returns to its precise original shape and thus squeezes the end of the vascular graft 33 tightly into the shallow groove 37. As a result of the precise tolerances, it is assured that the graft 33 cannot separate from the blood access device 31 without physically destroying either the coupling ring 39 or the rigid tubular end 35 of the device.

Depicted in FIG. 5 is a prosthetic application which demonstrates how an artificial tendon or ligament can be securely connected to a bone. Various materials have been developed for use as artifical tendons or ligaments, and multi-strand Dacron material that has been coated with vapor-deposited carbon shows particular promise for such applications. An expanded sleeve 41 of nickel-titanium alloy is provided as the coupling element, and one end 43 of a prosthetic tendon 45 is fed through the sleeve 41 and then through a hole that has been drilled through the bone 47 of the patient in an appropriate location. The free end 43 of the tendon is then passed back through the sleeve 41 in the opposite direction, as depicted in FIG. 6A.

The metal alloy is electrically conductive, and an appropriately insulated tool 49, shown diagrammatically in broken lines in FIG. 6B, which may generally resemble an electrically insulated pair of pliers, can be used to apply electric power to opposite locations on the sleeve 41. The flow of electric current resistively raise the temperature of the metal alloy above the transition-temperature range and thus causes the expanded sleeve 41 to return to its original shape where it squeezes or clamps the two portions of the artificial tendon 45 together in such a manner as to assure there can be no separation, as depicted in FIG. 6B. Thus, not only does the precision of the amount of compression which can be applied through the use of such a sleeve assure a very tight, permanent connection of the end 43 of the artificial tendon to itself, but also the fact that the metal alloy is electrically conductive allows it to be quickly heated by the simple application of electrical current after the connection with the bone has been made.

Depicted in FIG. 7 is an alternative embodiment of a valve body 51 which is generally similar to the valve body 13 shown in FIGS. 1 and 2. The body 51 is provided with a peripheral groove 53, the upper and lower edges of which are undercut. The fabric sewing ring to be installed similarly includes an outer covering 55 of a woven synthetic polymer fabric which is of a sufficient width so as to envelop a generally soft ring (not shown) of a semi-rigid polymer. A coupling element 57 is employed in the form of a relatively thin annular band which is sized to be snugly received against the flat wall of the undercut groove 53 with room provided to accommodate the thickness of the fabric 55.

The annular band 57, after cooling below its transition temperature, is expanded a sufficient amount to clear the exterior periphery of the valve body 51. The annular band is then deformed or folded into a generally U-shaped cross sectional configuration so that it will fit through the opening provided at the edge of the peripheral groove 53. As the coupling element 57 is heated, it shrinks in a circumferential direction while at the same time it expands (as depicted in an intermediate position in FIG. 7) from a U-shape cross section to a straight cross section, in which form it locks the covering 55 to the valve body 51. Instead of substantially expanding the coupling element 57 it could be formed as a split ring of approximately the proportion illustrated in FIG. 7. It could then be snapped or deformed into encircling relationship about the valve body and heated to return it to its flattened cross section. Even though such a ring would be split, as opposed to being continuous, it would have a significant advantage over a snap-ring or the like that relies upon spring action for its holding power and which would be inherently subject to stress corrosion problems.

Although the invention has been described with respect to certain preferred embodiments, it should be understood that various changes and modifications as would be obvious to one having the ordinary skill in the art may be made without departing from the scope of the invention which is defined solely by the appended claims. For example, although the specification speaks generally of heating the metal alloy to effect its return to it original shape, certain alloy compositions can be formed which have a transition-temperature range below ambient temperature. In such instances, the metal alloy is appropriately cooled, using a cryogen or other such source of refrigeration, to lower it to the temperature where it becomes ductile and deformation may take place. Then, simply by installing the coupling element while still cold, it can be allowed to simply warm to ambient temperature, causing it to return to its original shape as it passes through the transition-temperature range. Likewise, the temperature of end use of the product need not be above the transition temperature although the additional rigidity exhibited at such a temperature is an additional advantage. Various of the features of the invention are set forth in the claims that follow.

What is claimed is:

1. A prosthetic heart valve for long term implantation in the human body including
    a generally tubular rigid portion,
    a circumscribing sewing ring disposed in encircling relationship to said rigid tubular portion, and
    a coupling element embedded within said sewing ring for joining said sewing ring to said heart valve tubular portion wherein the improvement comprises
    said coupling element being made of a nickel-titanium alloy having a transition-temperature range, said element having been formed to a precise shape at a temperature above said range and having been deformed to a different shape at a temperature below said range whereby joinder of said sewing ring to said rigid tubular portion is effected by raising the temperature of said element above said range in order to cause said alloy to attempt to return to said precise shape.

2. A device in accordance with claim 1 wherein said coupling element is a continuous ring.

3. A device in accordance with claim 1 wherein the transition-temperature at which said metal alloy becomes ductile is about 20° C. or below.

* * * * *